(12) United States Patent
Friedl et al.

(10) Patent No.: US 6,734,393 B1
(45) Date of Patent: May 11, 2004

(54) DATA DISPLAY ON A WELDING SCREEN (75) Inventors: Helmut Friedl, Sipbachzell (AT); Franz Niedereder, Fischlham (AT); Heinrich Hackl, Ried/Traunkreis (AT)

(73) Assignee: Fronius International GmbH, Pettenbach (AT)

( * ) Notice: Subject to any disclaimer, the term of this patent is extended or adjusted under 35 U.S.C. 154(b) by 62 days.

(21) Appl. No.: 10/049,389
(22) PCT Filed: Aug. 11, 2000
(86) PCT No.: PCT/AT00/00219
§ 371 (c)(1), (2), (4) Date: Feb. 12, 2002
(87) PCT Pub. No.: WO01/12376
PCT Pub. Date: Feb. 22, 2001

(30) Foreign Application Priority Data

Aug. 13, 1999 (AT) ............................................. 1399/99

(51) Int. Cl.⁷ ................................................. B23K 9/10
(52) U.S. Cl. ................... 219/132; 219/130.01; 219/147
(58) Field of Search ................................ 219/147, 132, 219/130.5; 2/8

(56) References Cited

U.S. PATENT DOCUMENTS

| | | | | |
|---|---|---|---|---|
| 1,822,308 A | * | 9/1931 | Norton ........................ | 219/147 |
| 2,761,046 A | * | 8/1956 | Herrick et al. ............... | 219/147 |
| 3,692,974 A | | 9/1972 | Thomason et al. | |
| 3,792,226 A | * | 2/1974 | Bush ........................... | 219/147 |
| 4,555,614 A | * | 11/1985 | Morris et al. ............... | 219/147 |
| 4,638,146 A | * | 1/1987 | Koyama ..................... | 219/147 |
| 4,679,255 A | | 7/1987 | Kuhlman | |
| 4,863,244 A | * | 9/1989 | Fuerthbauer et al. ........... | 2/8 |
| 4,882,769 A | | 11/1989 | Gallimore | |
| 5,317,643 A | | 5/1994 | Patricelli | |
| 5,377,032 A | | 12/1994 | Fergason et al. | |
| 5,609,782 A | * | 3/1997 | Kim ........................... | 219/132 |
| 6,323,327 B1 | * | 11/2001 | Tzikas et al. ................. | 2/8 |

FOREIGN PATENT DOCUMENTS

| | | |
|---|---|---|
| DE | 35 36 678 | 7/1986 |
| DE | 40 37 879 | 6/1991 |
| DE | 296 02 946 | 5/1996 |
| DE | 196 21 664 | 7/1997 |
| EP | 0 963 744 | 6/1999 |
| JP | 09 098395 | 4/1997 |

* cited by examiner

*Primary Examiner*—Clifford C. Shaw
(74) *Attorney, Agent, or Firm*—Collard & Roe, P.C.

(57) ABSTRACT

The invention describes a welding system with a welding device (1) and a protective device (28), in particular a protective shield (29) for a user or welder. The protective device (28) has an electrically controllable and/or adjustable protective visor (31) with a control system (32). The welding device (1) or the welding system consists of at least one current source (2), a welding torch (10) and a control unit. The protective device (28) has a transmitter and/or receiver unit (33) which is connected to the control system (32). The transmitter and/or receiver unit (33) is connected to the welding system or the welding device (1) or the welding torch (10) via a connecting line (35) or alternatively wirelessly and, when a start switch (27) disposed on the welding torch (10) or on the welding device (1) is activated or when a start command is issued, the control unit or the welding torch (10) sends a signal via the transmitter and/or receiver unit (33) to the control system (32) to darken the protective visor (31).

23 Claims, 3 Drawing Sheets

DATA DISPLAY ON A WELDING SCREEN

CROSS REFERENCE TO RELATED APPLICATIONS

Applicants claim priority under 35 U.S.C. §119 of Austrian Application No. A 1399/99, filed on Aug. 13, 1999. Applicants also claim priority under 35 U.S.C. §365 of PCT/AT00/00219, filed on Aug. 11, 2000. The international application under PCT article 21(2) was not published in English.

The invention relates to a welding system with a welding device and a protective device, in particular a welding shield or a protective guard in the case of welding robots, as well as a method of controlling a welding system with a welding device and protective device and a method of displaying data or images, in particular welding parameters, on a protective shield.

A welding system with a welding device and a protective device, in particular a protective shield for a user, are known, in which the protective device is an electrically controllable protective visor with an activating device and the welding device consists of a power source, a welding torch and a control system. In this type of welding system, the protective visor is independently or automatically darkened, for which purpose a light-sensitive sensor is provided in the visor. When an arc is struck during a welding process, it is detected by the sensor due to the high intensity of light from the arc, whereupon a signal is sent from the sensor to the control system. Current and voltage are then applied by the control system and the protective visor is darkened.

The disadvantage of this system is that in order to initiate darkening of the protective visor, the arc has first to be struck, which means that the user is exposed to the full intensity of the arc for a brief moment, which can cause damage to the eyes of the user or welder.

A welding system and a welding device are also known from DE 296 02 946 U1, in particular a welding shield to shield against a welding process or an arc, in which the protective device is provided in the form of a handle with a protective shield and a transparent visor disposed in the protective shield. The protective device is connected by cable or wire or else wirelessly to an electronically controllable welding current source or a welding device. In order to vary the current strength of the welding current and/or the welding wire feed, a signal transmitter is integrated in the protective device with the handle and the welder is able to operate the signal transmitter without taking his hand off the handle.

The disadvantage of this system is that the protective visor is very dark and in order to take a reading of the settings, the user must lift the visor off his face in order to be able to read the display elements on the welding device and on the welding current source or, not knowing the settings, will enter a setting via the sensor which can lead to welding errors or poor quality weld seams if incorrect welding parameters are set.

A protective device for the eyes is known from JP 09 098395 A, the protective device having a support frame so that it can be attached to a user, in particular the head, and having a protective shield in the region of the user's face, which is connected to the support frame of an image-generating device which generates a data and/or image display.

Protective devices are also known, in which in order to secure the protective device on the welder, the protective device has a support frame instead of the hand grip, enabling it to be pivotably mounted on the head of the user or welder.

The disadvantage of this is that because the protective visor is so dark, the user or welder has to remove the protective device in order to read the welding settings.

Another significant disadvantage of the known embodiments described above resides in the fact that in order for a user or welder wearing an electronic, controllable protective visor to be able to take a reading of the welding settings without removing the protective device from his face, he has to interrupt or terminate the welding process to switch off the darkening on the protective visor.

A display system and image-generating system for a helmet are described in DE 40 37 879 A1, the display system having a display unit on the inside face of the helmet for displaying information and data. The display light from the display unit is reflected by means of an internal face of the transparent visor disposed on the helmet to an observation position so that a user is able to see a virtual image from inside the helmet.

The disadvantage of this system is that a helmet of this type may not be used for protection purposes in welding processes.

The underlying objective of the invention is to propose a welding system with a welding device and a protective device, in particular a welding shield or a protective cover in the case of welding robots, as well as a method of controlling a welding system with a welding device and a protective device and a method of displaying data or images, in particular welding parameters, on a protective shield such that the user or welder is has unrestricted freedom of movement.

This objective is achieved by the invention due to the features defined in the characterising part of claim 1. The advantage of this system is that the control system initiates and terminates the procedure to darken the protective visor prior to igniting the arc by transmitting a signal, so that the welder, in particular the welder's eyes, are protected from the arc. Another advantage is the fact that if using wireless signal transmission, there are no restrictions on the movements of the welder.

An embodiment of the type defined in claim 2 is of advantage because the protective device is coupled with the welding system and welding device and it is a simple matter to adapt the darkening procedure to the different welding processes because the degree of darkening can be easily set from the control system, thereby simplifying the circuitry of the activating device for the protective visor in the protective device and bringing a considerable weight saving.

Another embodiment defined in claim 3 is of advantage since it allows the protective device to be used without connecting it to the welding system or welding device.

Advantage is to be had from another embodiment defined in claim 4, because once the welding process has been terminated, in particular once the arc has been switched off, the protective visor is de-activated and the darkening on the protective visor removed.

The objective is also achieved by the invention as a result of the features set out in the characterising part of claim 5. The advantage of this approach is that, even once the protective visor has been darkened, the welder is still able to see the most important welding parameters and adjust a welding parameter without the welding process having to be interrupted in order to be able to read the correction value. Another significant advantage resides in the fact that by generating a virtual data and/or image display, different operating statuses of the welding process may also be displayed to the welder, such as a short circuit, stable arc, arc ignition, etc., enabling the welding process to be accurately monitored and controlled, thereby improving the welding quality.

Claim 6 describes an advantageous embodiment whereby an automatic darkening process can be run and a virtual data and/or image display of the welding parameters and/or the welding process obtained at the same time.

The embodiments defined in claims 7 to 14 also offer advantages since, by using a video camera or an optical recording unit, a virtual image can be generated in real time and an image of the surroundings and/or the welding process will be displayed for the welder in such a way that the image will change depending on the head movement of the welder, obviating the need constantly to remove the protective device.

The invention additionally relates to a method of controlling a welding system with a welding device and a protective device of the type described in the generic part of claim 15.

This objective is achieved by the invention as a result of the features set out in the characterising part of claim 15. The advantage of this system is that it provides a simple means of transferring data and exchanging data between the welding system and the protective device, thereby enabling the darkening switch of the protective device to be controlled depending on the welding process.

The features described in claims 16 to 19 are also of advantage since they ensure that the protective visor is darkened before the arc is ignited and the darkening system of the protective device can be switched oft once the welding process has ended.

The objective is also achieved by the invention as a result of the features set out in the characterising part of claim 20. The advantage of this system is that by forming a virtual data and/or image display, the welder is able to take readings of specific welding parameters at all times, even if the protective visor is darkened. Another advantage resides in the fact that in welding systems in which the welding device can be placed farther away from the welding point, the welder is able to read the settings via the protective device and will no longer have to run test welds and will no longer have to go backwards and forwards from the welding device.

Finally, the features defined in claims 21 to 23 are of advantage because they give the welder or user the option of being able to display on the protective device those welding parameters which are more important for him.

The invention will be described in more detail below with reference to examples of embodiments illustrated in the appended drawings.

Of these.

Firstly, it should be pointed out that the same reference numbers are used to denote the same parts in the individual embodiments. The positions described in the individual examples of embodiments may be transposed to new positions in terms of meaning when other positions are being described.

Figure 1:
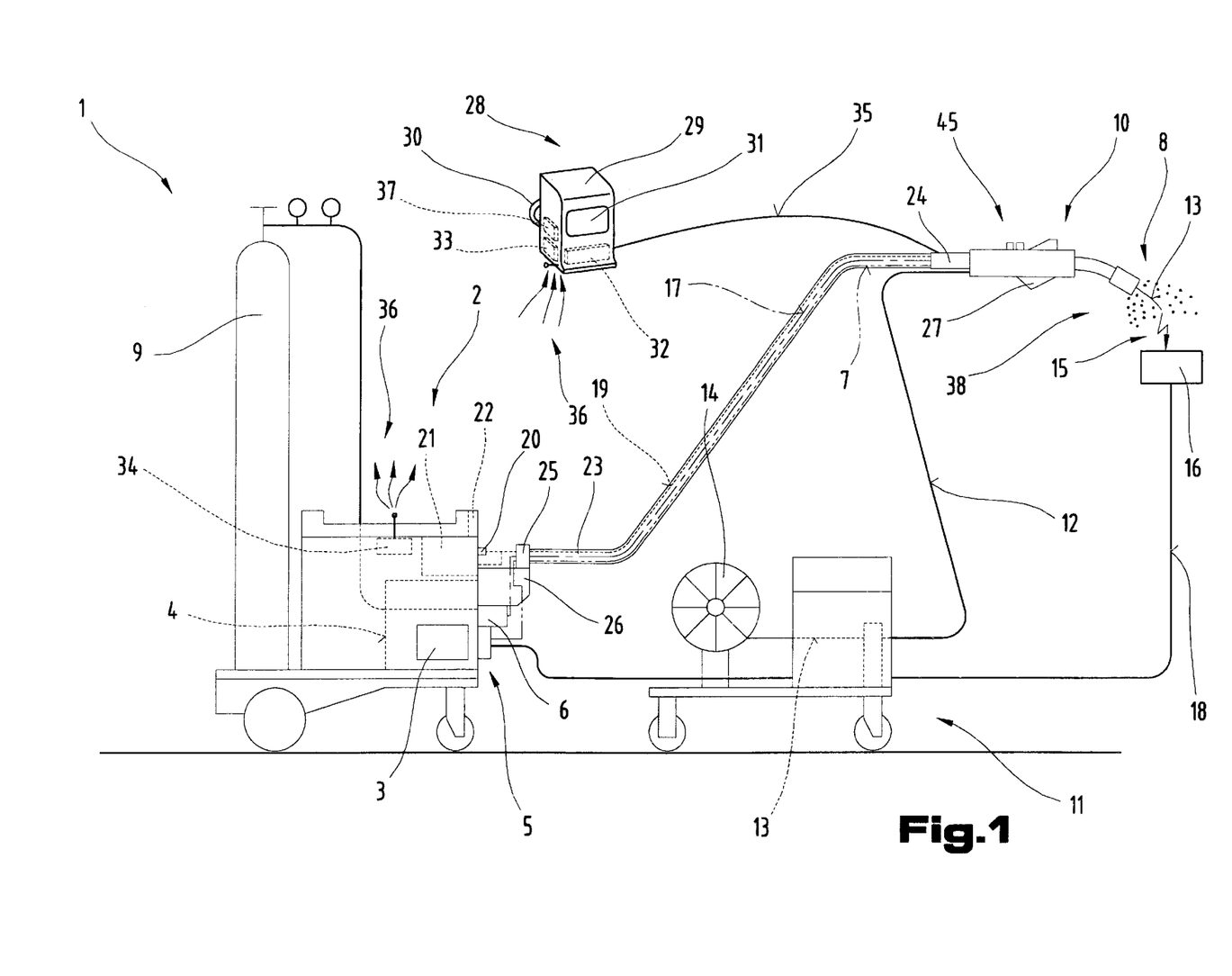
FIG. 1 is a simplified, schematic diagram of a welding machine or a welding device with a protective device as proposed by the invention.
Figure 2:
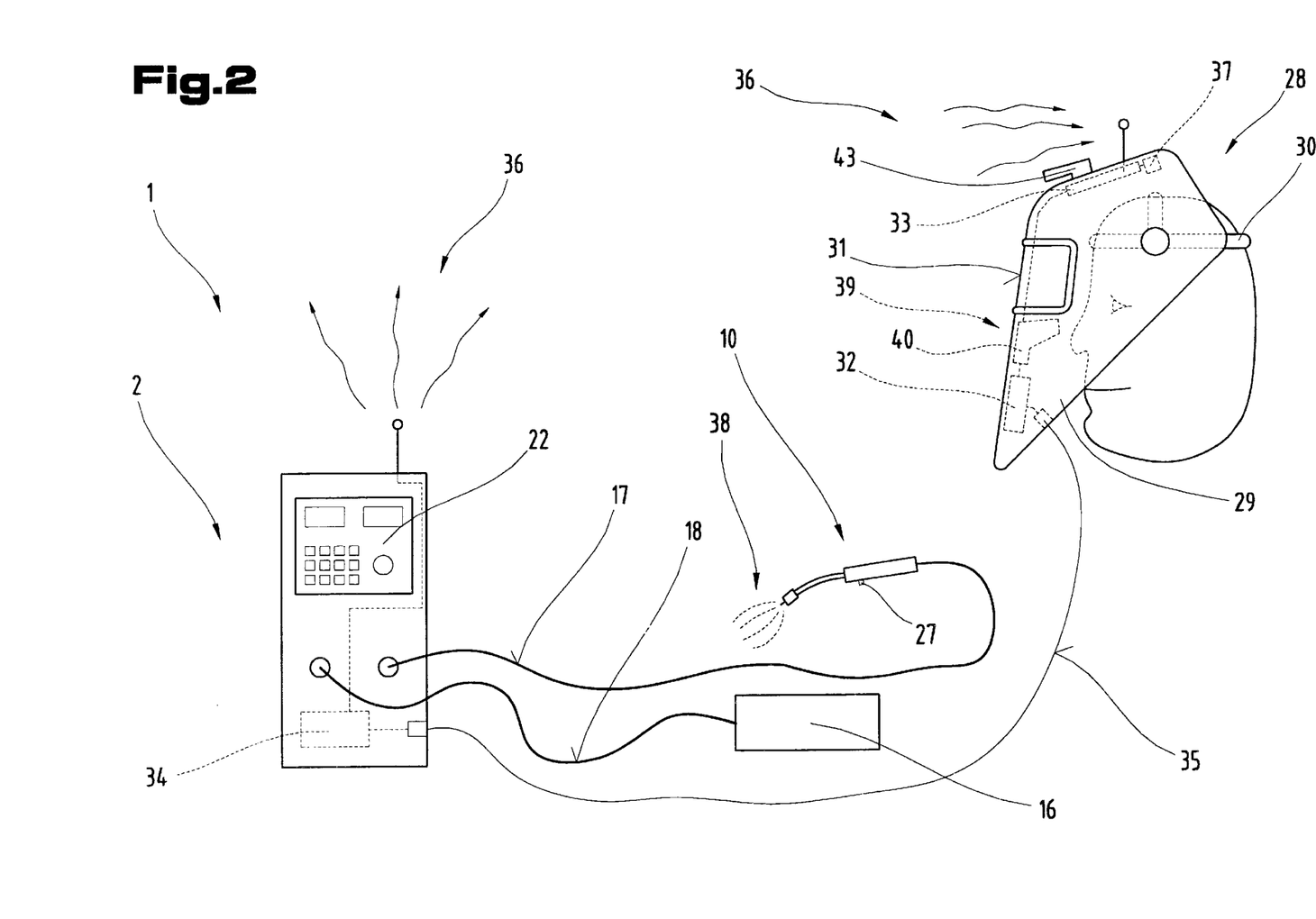
FIG. 2 is another simplified, schematic diagram of the welding system fitted with the protective device proposed by the invention.
Figure 3:
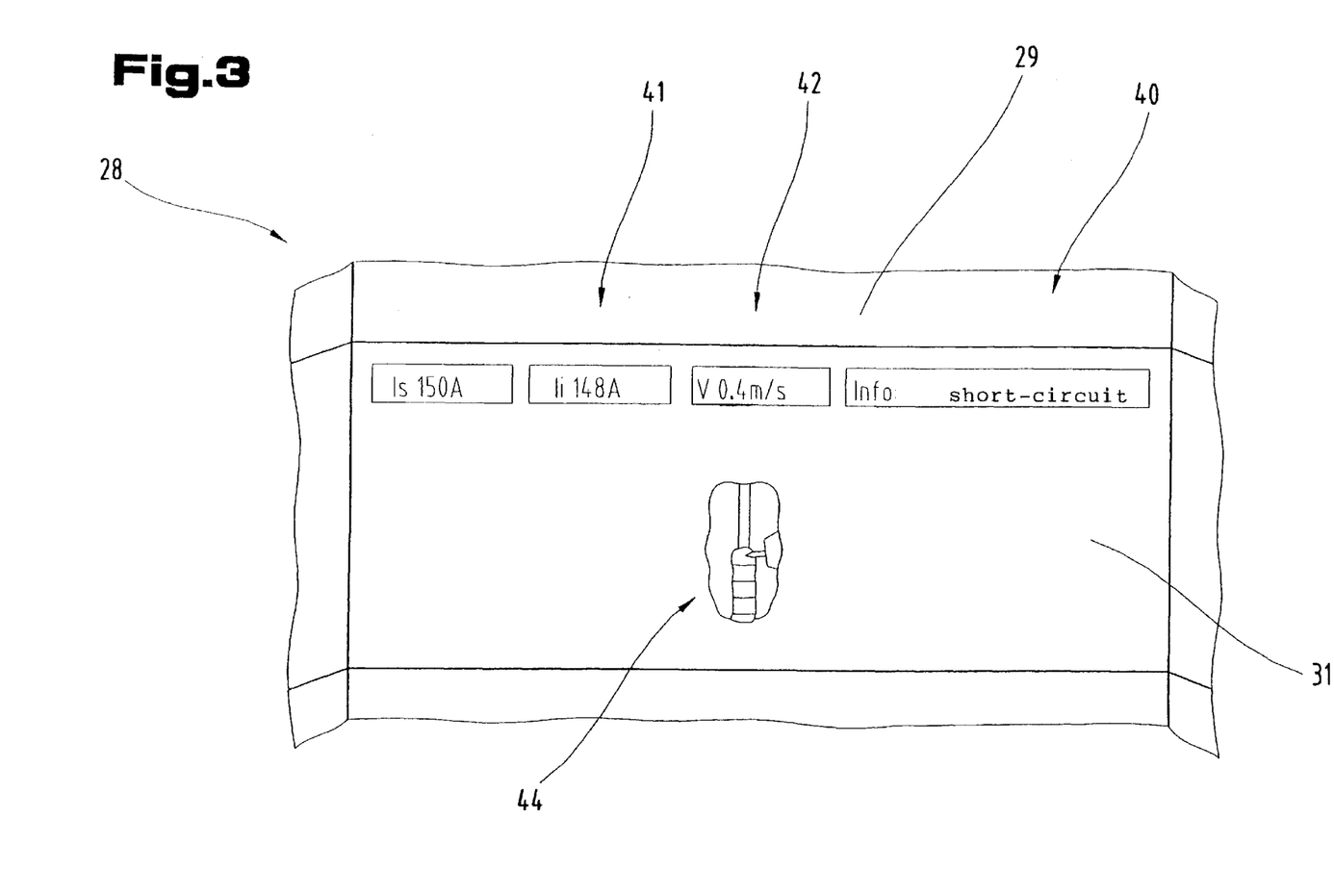
FIG. 3 is a simplified, schematic diagram showing the view which a welder has of the protective device proposed by the invention.

FIGS. 1, 2 and 3 illustrate a welding system or welding device 1 for running a whole variety of welding processes, e.g. MIG/MAG welding and TIG welding or electrode welding, with or without an inert gas atmosphere. Clearly, the solution proposed by the invention may also be used with a current source or a welding current source.

The welding device 1 comprises a current source 2 with a power component 3, a control unit 4 and a switching element 5 co-operating with the power component 3 or control unit 4. Connected to the switching element 5 or the control unit 4 is a control valve 6, disposed in a supply line 7 for a gas 8, in particular an inert gas such as $CO_2$, helium or argon or similar, between a gas storage 9 and a welding torch 10.

A wire feed device 11, such as commonly used in MIG/MAG welding for example, may also be activated via the control unit 4, in which case a welding wire 13 will be fed from a supply drum 14 via a supply line 12 into the region of the welding torch 10. Clearly, the wire feed device 11 could also be integrated in the welding device 1, in particular in the basic housing, in a manner known from the prior art, instead of being provided as a separate device.

The current needed to generate an arc 15 between the welding wire 13 and a workpiece 16 is fed via a welding line 17 from the power component 3 to the welding torch 10 and the welding wire 13, the workpiece 16 to be welded also being connected to the welding device 1, in particular to the power component 3, via another welding line 18, thereby enabling a circuit to be established across the arc 15.

In order to cool the welding torch 10, a liquid container, in particular a water container 21, may be connected to the welding torch 10 via a cooling circuit 19, with a flow indicator 20 connected in between, so that when the welding torch 10 is switched on, the cooling circuit 19, in particular a fluid pump for the liquid disposed in the water container 21, is activated in order to cool the welding torch 10 or welding wire.

The welding device 1 additionally has an input and/or output device 22, by means of which a whole range of welding parameters or operating modes of the welding device 1 can be set.

The welding parameters entered at the input and/or output device 22 are forwarded to the control unit 4, which then activates the individual components of the welding system or welding device 1.

In the embodiment illustrated as an example here, the welding torch 10 is connected via a hose pack 23 to the welding device 1 or welding system. Disposed in the hose pack 23 are the individual lines running from the welding device 1 to the welding torch 10. The hose pack 23 is connected to the welding torch 10 by means of a connecting device 24 known from the prior art, whilst the individual lines in the hose pack 23 are connected to the individual contacts of the welding device 1 by means of connector sleeves or socket connectors. To relieve tension on the hose pack 23, the hose pack is connected to a housing 26, in particular the basic housing of the welding device 1, via a tension-relieving device 25.

To enable a welding process to be started by the user or welder, a start switch 27 is provided on the welding torch 10, i.e. when the welder activates the start switch 27, a signal is generated which is forwarded via at least one line to the control unit 4, so that the control unit 4 detects that a welding process is to be initiated and an arc ignited and all the other requisite process steps, such as starting the gas feed, igniting the arc, activating the wire feed device 11, etc., can be started by the control unit 4. These individual method steps are already known from the prior art and will therefore not be described in more detail here. Clearly, the start switch 27 could be arranged alternatively or additionally on the input and/or output device 22.

In order to protect the welder, in particular his eyes, from the arc 15, especially the highly intense light from the arc 15 and/or any spattering which might occur during the welding process, the welder uses an appropriate protective device 28, in particular a protective shield 29 which, in a manner known from the prior art, may be secured on the head of the welder by means of a support frame 30 or can be held in front of the face, in particular the eyes, by means of a handle.

In the welding system with the welding device 1 and the protective device 28, in particular the protective shield 29 for the user or welder, illustrated here, the protective device 28 has an electrically controllable protective visor 31 with a control system 32, i.e. the protective visor 31 is one whereby, when power is applied, in particular current and voltage, the protective visor 31 is darkened in order to protect the user from the intense light of the arc 15, in a manner known per se.

Accordingly, the control unit 4 runs a control process for a welding system and a welding device 1 and the protective device 28, in particular the protective shield 29 for the user, such that when the start switch 27 is operated, from the welding torch 10 or the welding device 1 for example, a start signal is generated at the control unit 4 of the welding device or a current source in order to initiate a welding process, and, on activation of the start switch 27, a signal or radio signal or start command is transmitted via a transmitter and/or receiver unit 33 and 34 to the control system 32 of the protective device 28, whereupon the control system 32 applies energy to activate an electrically controllable and/or adjustable protective visor is activated before the welding process is started, in particular ignition of the arc, preferably after the elapse of a pre-settable run-in time and/or gas run-in time, during which the protective visor is darkened. One option is to set up the system so that the arc is not ignited by the control unit 4 until a response has been received from the control system which will involve simply sending a response signal via the receiver and/or transmitter system 33, which will ensure that the protective visor is already dark prior to ignition.

With the protective devices 28 or control methods known from the prior art, a light-sensitive sensor is connected to the control system 32 for this purpose and the sensor is activated by the strong intensity of light generated when the arc 15 is ignited, despatching a signal to the control system 32 which then applies energy to the protective visor 31.

The protective device 28 proposed by the invention has a transmitter and/or receiver unit 33, which is connected to the control system 32. The transmitter and/or receiver unit 33 is connected to the welding system or the welding device 1 or welding torch 10 via a connecting line 35, for example, as schematically shown on the welding torch 10, or wirelessly, the connecting line 35 for sending a signal to the transmitter and/or receiver unit 33 being connected, directly or indirectly, in particular via a field bus, to the control unit 4. If the protective device 28 is wirelessly connected to the welding system, the current source 2 or the welding device 1, in particular the welding torch 10, the transmitter and/or receiver unit 33 for receiving radio signals is of the type based on electromagnetic waves or optical, preferably infrared signals.

To this end, at least one component, in particular the welding device 1, has another compatible transmitter and/or receiver unit 34, as indicated by the broken lines in the basic housing 26, so that a data exchange can be run or a radio signal 36 or control signal transmitted. Clearly, both systems may be used, in other words a hard-wired and a wireless connection, in which case the welder will be able to select the connection type.

In order to be able to feed energy to the components disposed in the protective device 28, in particular the transmitter and/or receiver unit 33 and the control system 32, if the protective device 28 is wirelessly connected to the welding device 1, the protective device 28 has its own energy source 37, in particular a battery and/or a solar cell, in which case power may also be drawn from the energy source 37 to control the protective visor 31.

When a user or welder activates the start switch 27 at the start of a welding process, a signal or start command is transmitted to the control unit 4, whereupon the control unit 4 activates the individual start procedures. First of all, the control valve 6 is activated by the control unit 4 so that an inert gas atmosphere 38 is built up around the welding wire 13 at the welding torch 10 during a gas run-in time. At the same time as the gas run-in time is initiated, the control unit 4 sends a radio signal 36 or control signal via the transmitter and/or receiver unit 33 and 34 to the control system 32, prompting the control system 32 to activate the darkening procedure for the protective visor 31, i.e. the control system 32 starts applying energy to the protective visor 31.

Activating the gas run-in time and the darkening procedure for the protective visor 31 simultaneously ensures that the protective visor 31 is darkened before the arc 15 is ignited, preventing any harm to the welder such as can occur with the darkening methods known from the prior art.

Another option available with a procedure or control method of this type is to transmit different signals or radio signals 36 to the control system 32, from the control unit 4 or directly from the welding torch 10 depending on pre-set welding parameters, in particular a welding current, so that the control system 32 will determine the degree to which the protective visor 31 is darkened on the basis of the received signal, i.e. different parameters, in particular the level of the welding current, can be used to adapt to the resultant light intensity, allowing the degree of darkening for the protective visor 31 to be controlled. The advantage of this is that if the light intensity is low, darkening can be adjusted to a lower level and the welder can continue the welding process without any sight problems. Furthermore, the run-in time and/or the gas run-in time can be set by the control unit 4 depending on the set welding parameters, so that different timing is available for darkening the protective visor in order to ensure that the process of darkening the protective visor 31 is terminated before the arc 15 is ignited. Once the gas run-in time set by the control unit 4 has elapsed and hence the darkening process run, the control unit 4 starts the welding process, in other words ignites the arc 15. Once the welder has completed the welding process, i.e. the arc 15 is extinguished, this fact is detected by the control unit 4 so that a new signal or radio signal 36 or start command is transmitted to the control system 32 in order to deactivate the protective visor 31, and the power supply to the protective visor 31 is interrupted and the darkening of the protective visor 31 removed. However, it is also of advantage if, when the arc 15 is broken, a run-down time is initiated by the control unit 4 and the darkening on the protective visor 31 is not lifted until this run-down time has elapsed. The purpose of this is that in the event of a short circuit between the electrode, in particular the welding wire 13, and the workpiece 16, the degree of darkening is not removed leaving a situation in which the darkening is not active on re-ignition. The run-down time could also be used as a gas run-down time which means that the inert gas atmosphere 38 would still be maintained on completion of the welding process.

Another possibility is for an image-generating device 39 to be provided in the protective device 28, in particular the protective shield 29, or on a protective guard in the protective shield 29 in the case of a welding robot or welding automation and/or to be connected to the support frame 30, in order to generate a data and/or image display 40 of adjustable welding parameters and/or welding process images in the region of the protective visor 31, of the type known from the introductory description to patent document DE 40 37 879 A1. This being the case, as may be seen from FIG. 3, the welding parameters for the welding current 41 and the wire feed rate 42 could be displayed. Clearly, it would also be possible for a plurality of welding parameters to be displayed.

Naturally, it would be possible for the protective device 28 to be equipped with only the image-generating device 39 and the energy source 37, in which case the connection to a component of the welding system or the welding device 1 could be provided in the form of a wireless and/or hard-wired link.

The image-generating device 39 may in turn be connected to the transmitter and/or receiver unit 34 and the energy source 37, consisting of the battery and/or the solar cell disposed on the protective visor 31, or to the control 32. The virtual image generated by the image-generating device 39, in particular the data and/or image display 40, forms a part region of the protective visor 31, i.e. a virtual image is projected onto the protective visor 31 but in such a way that the welder can continue the welding process in spite of the image.

The virtual image is formed by the display of fixed welding parameters on the welding device 1 or on the welding system or another input device, i.e. these welding parameters are transmitted from the control unit 4 via the transmitter and/or receiver units 33 and 34 to the protective device 28 and then forwarded to the image-generating device 39 so that a virtual image corresponding to the set desired values and/or actual values of the welding parameters can be displayed. The virtual image may be of any structure since any image-generating device 39 known from the prior art may be used.

In addition to or independently of the method described above, a method of displaying data or images, in particular welding parameters, on the protective device 28, in particular the protective shield 29 may be run, so that the user or welder can adjust individual welding parameters for a welding process via the input and/or output device 22 on the welding system or welding device 1, in which case data relating to at least one fixed welding parameter is transmitted from the transmitter and/or receiver unit 34 arranged in the welding device 1 to the other transmitter and/or receiver unit 33 disposed in the protective device 28, in particular the protective shield 29 or a protective guard, and this data is then forwarded to the image-generating device 39 so that the image of the welding parameters and/or a welding process can be generated on the protective device 28 by the data and/or image display 40. This being the case, data is continuously or periodically transferred between the welding system or welding device 1 and the protective device 28 or protective shield or vice versa so that a real time display of the desired values and/or actual values for the welding parameters can be produced.

Similarly, a video camera or another optical recording device 43 may be provided in the protective shield, as schematically indicated, positioned so that it overlaps with the range of vision of the protective visor 31 of the user or welder and generates a corresponding image 44 of the surroundings or welding process in real time, which can then be forwarded to the image-generating device 39. Consequently, another virtual image 44 containing data from the video camera or optical recording device 43 can be produced in the range of the protective visor 31, it being possible for the protective visor 31 to be non-transparent because a corresponding image 44 produced via the optical recording device 43 can be made visible to the welder by the virtual image-generating device 39.

The advantage of this of this design of the protective device 28 for generating a virtual data and/or image display 40 in the region of the protective visor 31 is that when the protective visor 31 is darkened, the user will be able to see the most important welding parameters at all times, which will enhance the welding quality of the weld seam given that it will be possible to actively intervene in the welding process as and when variances occur. To this end, it would naturally be possible to provide setting elements 45 on the protective device 28 or on the welding torch 10, enabling the welding parameters to be adjusted or the welding process to be interrupted. This being the case, the setting elements 45 are such that they match the displayed welding parameters, i.e. at least one setting element 45 is provided on the welding torch 10 which is capable of adjusting each and every welding parameter.

This setting element 45 would be set up to co-operate with the control unit 4, depending on the welding parameter on the protective shield 29, so that the desired value of the welding parameter is altered when the setting element 45 is operated, and this would be transferred in real time to the image-generating device 39 enabling the welder to take a reading of the change made. Naturally, a plurality of setting elements 45 may be provided or one setting clement 45 and one selector so as to select different welding parameters. The advantage of this is that a compact structure is obtained which simultaneously allows any selection of possible settings to be made. If the welder selects a welding parameter that was not previously selected for display on the protective visor 31, this welding parameter will be sent by the control unit 4 to the image-generating device 39 for display on the protective shield 29 and the welder will now be able to see and take a reading of the new welding parameter, in particular the actual or desired value and an abbreviated code stored for this particular welding parameter.

Furthermore, the user or welder is free to set the position from where the welding parameters are displayed, i.e. in a manner known from the prior art, the welder will be able to set the position at which the virtual image will be displayed using setting elements on the protective shield 29 or by simply touching the protective visor 31, so that the virtual image 44 generated by the image-generating device 39 is produced within the range of the user's eyes, in which case the virtual image 44 of the data and/or image display 40 on the welding device 1, in particular the individual welding parameters to be displayed, will also be freely selectable. The same is also possible using the video camera or optical recording device 43 integrated in the protective shield 31, from which a continuous image 44, in particular a welding image of the welding process, can be recorded and forwarded to the image-generating device 39, enabling the image-generating device 39 to generate another image 44 within the range of the eyes. Naturally, it would also be possible to use one or more image-generating devices 39 to generate several virtual images on the protective device 38, particularly in the region of the protective visor 31.

Finally, it should be pointed out that the individual parts and components or component units described in the examples of embodiments are illustrated in a schematic or simplified form. Individual parts of the combinations of features described above with respect to the individual embodiments may be used in combination with other individual features from other embodiments and be construed as independent solutions of the invention in their own right.

Above all, subject matter relating to the individual embodiments illustrated in FIGS. 1, 2, 3 can be construed as independent solutions proposed by the invention. The tasks and solutions can be found in the detailed descriptions relating to these drawings.

| | List of reference numbers |
|---|---|
| 1 | Welding device |
| 2 | Current source |
| 3 | Power component |
| 4 | Control unit |
| 5 | Switching element |
| 6 | Control valve |
| 7 | Supply line |
| 8 | Gas |
| 9 | Gas storage |
| 10 | Welding torch |
| 11 | Wire feed device |
| 12 | Supply line |
| 13 | Welding wire |
| 14 | Supply drum |
| 15 | Arc |
| 16 | Workpiece |
| 17 | Welding line |
| 18 | Welding line |
| 19 | Cooling circuit |
| 20 | Flow indicator |
| 21 | Water container |
| 22 | Input and/or output device |
| 23 | Hose pack |
| 24 | Connecting unit |
| 25 | Tension-relieving device |
| 26 | Housing |
| 27 | Start switch |
| 28 | Protective device |
| 29 | Protective shield |
| 30 | Support frame |
| 31 | Protective visor |
| 32 | Control system |
| 33 | Transmitter and/or receiver system |
| 34 | Transmitter and/or receiver system |
| 35 | Connecting line |
| 36 | Radio signal |
| 37 | Energy source |
| 38 | Inert gas atmosphere |
| 39 | Image-generating device |
| 40 | Data and/or image display |
| 41 | Welding current |
| 42 | Wire feed rate |
| 43 | Recording device |
| 44 | Image |
| 45 | Setting element |

What is claimed is:

1. A welding system comprising a current source, a welding device, a control unit, a starting switch, and a protective device for a user, the protective device having a protective visor with a control system for electrically controlling the protective visor and a transmitter/receiver unit connected to the control system, the transmitter/receiver unit being also connected by a connecting line or wirelessly to the welding torch, and the starting switch being adapted, upon actuation, to cause the control unit to send a starting signal via the transmitter/receiver unit to the control system to darken the protective visor and, after a pre-settable run-in time or gas run-in time, to initiate a welding process.

2. Welding system as claimed in claim 1, wherein the control unit transmits different signals to the control system, depending on pre-set welding parameters, and the control system sets the degree of darkening for the protective visors, depending on the transmitted signal.

3. Welding system as claimed in claim 1, comprising an energy source in the protective device.

4. Welding system as claimed in claim 1, wherein the control unit transmits an updated signal via the transmitter receiver unit to the control system in order to de-activate darkening of the protective visor when the welding process is completed.

5. Welding system as claimed in claim 1, wherein an image-generating device is integrated in the protective device which generates a data and/or image display of at least one of the welding parameters and/or a welding process image in the region of the protective visor.

6. Welding system as claimed in claim 5, wherein the image-generating device is connected to the transmitter receiver unit and an energy source.

7. Welding system as claimed in claim 1, wherein the transmitter receiver unit is connected wirelessly or via a connecting line to another transmitter receiver unit disposed in the welding device.

8. Welding system as claimed in claim 1, wherein a virtual image or a data and/or image display generated by an image-generating device integrated in the protective device forms a part region of the protective visor.

9. Welding system as claimed in claim 8, wherein the virtual image or the data and/or image display may be freely selected from the welding device.

10. Welding system as claimed in claim 8, wherein the virtual image or the data and/or image display is based on pre-set desired values and/or actual values of the welding parameters.

11. Welding system as claimed in claim 1, comprising a video camera or another optical recording device in the protective device which is positioned so that it overlaps with the range of vision of the protective visor of the user and generates a corresponding image in real times, which is forwarded to an image-generating device which produces virtual image with the data from the video camera or the optical recording device in the region of the protective visor.

12. Welding system as claimed in claim 1, wherein the protective device is designed so that it may be used with a welding robot as a protective guard.

13. A control method for a welding system comprising a current source, a welding device, a control unit, a starting switch, and a protective device for a user, the protective device having a protective visor with a control system for electrically controlling the protective visor and a transmitter/receiver unit connected to the control system, the transmitter/receiver unit being also connected by a connecting line or wirelessly to the welding torch, the control method comprising the step of causing the control unit, upon actuation of the starting switch, to send a starting signal via the transmitter/receiver unit to the control system to darken the protective visor and, after a pre-settable run-in time or gas run-in time, to initiate a welding process by igniting of an arc.

14. Control method as claimed in claim 13, wherein the run-in time or the gas run-in time is set by the control unit dependent on welding parameter settings.

15. Control method as claimed in claim 14, wherein the degree to which the protective visor is darkened is set depending on the welding parameter settings, a corresponding signal being sent from the control unit to the protective device.

16. Control method as claimed in claim 13, wherein a more up-to-date signal is sent from the control unit to interrupt the energy supply to the protective visor by the control system when the welding process is terminated.

17. Control method as claimed in claim 13, wherein data pertaining to at least one fixed welding parameter is sent from a transmitter receiver unit disposed in the welding device to another transmitter receiver unit disposed in the protective device, which then transmits these data to an image-generating device, which uses them to generate a data and/or image display of the welding parameter and/or a welding process image on the protective device.

18. Control method as claimed in claim 13, wherein a continuous or periodic data transfer is operated between the welding system and the protective device.

19. Control method as claimed in claim 13, wherein welding parameters to be displayed are set via an input device by the user.

20. Control method as claimed in claim 19, wherein the position of the display of the welding parameters is freely selected by the user.

21. Control method as claimed in claim 13, wherein a virtual image is generated by an image-generating device in the region of the eyes of the user.

22. Control method as claimed in claim 21, that wherein a continuous image is recorded by a video camera or optical recording device disposed in the protective device and forwarded to the image-generating device, as a result of which another image is produced by the image-generating device in the region of the eyes.

23. Control method as claimed in claim 21, wherein several virtual images are produced on the protective device by one or more image-generating devices.

* * * * *

UNITED STATES PATENT AND TRADEMARK OFFICE
CERTIFICATE OF CORRECTION

PATENT NO. : 6,734,393 B1
DATED : May 11, 2004
INVENTOR(S) : Friedl et al.

It is certified that error appears in the above-identified patent and that said Letters Patent is hereby corrected as shown below:

Title page,
Item [56], References Cited, U.S. PATENT DOCUMENTS, "6,323,327 B1 * 11/2001 Tzikas et al…...2/8" should read -- 6,230,327 B1 5/01 Briand Et Al……...2/8 --.

Signed and Sealed this

Twenty-seventh Day of July, 2004

JON W. DUDAS
*Acting Director of the United States Patent and Trademark Office*